(12) United States Patent
Giddings et al.

(10) Patent No.: US 8,641,642 B2
(45) Date of Patent: Feb. 4, 2014

(54) BIOLOGICAL SAMPLE COLLECTION SYSTEM

(75) Inventors: Jason Giddings, Forest Grove, OR (US); Paul D Slowey, Vancouver, WA (US)

(73) Assignee: Oasis Diagnostics Corporation, Vancouver, WA (US)

( * ) Notice: Subject to any disclaimer, the term of this patent is extended or adjusted under 35 U.S.C. 154(b) by 0 days.

(21) Appl. No.: 13/576,128

(22) PCT Filed: Feb. 1, 2011

(86) PCT No.: PCT/US2011/023370
§ 371 (c)(1),
(2), (4) Date: Jul. 30, 2012

(87) PCT Pub. No.: WO2011/094745
PCT Pub. Date: Aug. 4, 2011

(65) Prior Publication Data
US 2012/0310113 A1 Dec. 6, 2012

Related U.S. Application Data

(63) Continuation-in-part of application No. 12/628,893, filed on Dec. 1, 2009.

(60) Provisional application No. 61/300,419, filed on Feb. 1, 2010, provisional application No. 61/118,911, filed on Dec. 1, 2008.

(51) Int. Cl.
*A61B 10/00* (2006.01)
*A61B 5/00* (2006.01)

(52) U.S. Cl.
USPC .......................................... 600/570; 600/572

(58) Field of Classification Search
USPC .......................... 600/562, 569, 570, 572, 573
See application file for complete search history.

(56) References Cited

U.S. PATENT DOCUMENTS

| | | | |
|---|---|---|---|
| 3,766,907 A | 10/1973 | Muenzer | |
| 3,800,781 A | 4/1974 | Zalucki | |
| 3,838,681 A | 10/1974 | Dalton | |
| 4,641,662 A * | 2/1987 | Jaicks | 600/570 |
| 4,741,346 A | 5/1988 | Wong et al. | |
| 4,951,684 A | 8/1990 | McMillan | |
| 5,063,026 A | 11/1991 | Wong | |
| 5,231,992 A * | 8/1993 | Leon | 600/572 |
| 5,422,273 A | 6/1995 | Garrison et al. | |
| 5,919,146 A | 7/1999 | Propp | |
| 6,174,293 B1 * | 1/2001 | Buck et al. | 600/572 |

(Continued)

OTHER PUBLICATIONS

KR 10-0662124 B1, Rapid Medical Diagnostics Corporation, Dec. 27, 2006, pp. 4-6, claim 1 and Figs. 1-24.

*Primary Examiner* — Max Hindenburg
*Assistant Examiner* — Jonathan M Foreman
(74) *Attorney, Agent, or Firm* — Rylander & Assoc. PC; Mark E. Beatty; Kurt M. Rylander (57) ABSTRACT

A biological sample collection system is described comprising a biological sample collecting wand and a buffer container with a buffer solution. The biological sample collecting wand includes a handle and a sample collector detachably coupled to the handle. The sample collector include one or more sample protrusions, one or more sample apertures, or a combination thereof, at least the sample collector to removably insert into the buffer container.

19 Claims, 9 Drawing Sheets

(56) References Cited

U.S. PATENT DOCUMENTS

| | | |
|---|---|---|
| 6,200,276 B1 | 3/2001 | Biesel et al. |
| 6,299,842 B1 | 10/2001 | Kozak et al. |
| 6,312,395 B1 | 11/2001 | Tripp et al. |
| 6,840,911 B2 | 1/2005 | Sangha |
| 7,257,991 B2 | 8/2007 | Wickstead et al. |
| 2003/0021736 A1 | 1/2003 | Kang et al. |
| 2004/0181170 A1 | 9/2004 | Wallach |
| 2004/0260194 A1 | 12/2004 | Bayer et al. |
| 2005/0096563 A1 | 5/2005 | Liang |
| 2006/0047292 A1 | 3/2006 | Reed |
| 2006/0149164 A1 | 7/2006 | Lee et al. |
| 2007/0073186 A1* | 3/2007 | Decker et al. ............ 600/569 |
| 2007/0208274 A1 | 9/2007 | Ostrowski et al. |
| 2008/0118397 A1 | 5/2008 | Slowey et al. |
| 2008/0262384 A1* | 10/2008 | Wiederkehr et al. ........ 600/569 |
| 2009/0012425 A1 | 1/2009 | Dodge et al. |
| 2009/0038416 A1 | 2/2009 | Bonner |
| 2009/0208371 A1 | 8/2009 | Hannant et al. |

\* cited by examiner

BIOLOGICAL SAMPLE COLLECTION SYSTEM

CROSS-REFERENCE TO RELATED APPLICATION

This application claims priority to U.S. Provisional Patent Application Ser. No. 61/300,419 filed Feb. 1, 2010, incorporated herein by reference.

FIELD OF THE INVENTION

The present invention relates to devices for collecting biological samples by scraping the surface of a body part.

BACKGROUND

Over the last few years there has been a tremendous growth in the area of salivary diagnostics, prompted in part by efforts from the National Institutes of Health (NIH) and its National Institute of Dental and Craniofacial Research (NIDCR) division to promote the development of non-invasive technologies for the diagnosis of diseases and measurement of specific analytes or molecules in saliva or oral fluid samples. These agencies have made funding available for the development of novel, innovative tools including microarrays, lab-on-a-chip, lateral flow, ELISA and other technologies using saliva and other non-invasive sampling methodologies. Other reasons for the increased interest in salivary diagnostics include the development of important new technologies for both the collection and testing of oral fluids and improvements in the manufacturability of such devices.

There are several successful corporate stories in salivary diagnostics that are also prompting other companies to search out opportunities in non-invasive testing. For instance, it is now possible to detect HIV antibodies from oral specimens at the point-of-care using the OraQuick® HIV 1/2 rapid antibody test (OraSure Technologies, Bethlehem Pa., USA) with greater than 99% sensitivity and specificity. This company is currently proceeding with an FDA submission that would allow consumers to purchase such a test over the counter in a pharmacy.

In the United States millions of oral specimens are collected and processed in the Public Health and insurance market sectors for HIV antibodies, cotinine (nicotine) for smoking and cocaine as part of a "risk assessment" profile. Additionally, options for testing Federal employees for a range of abused drugs using non-invasive methods including saliva are readily accepted by SAMHSA, the Substance Abuse Mental Health Services Administration (the US Government body responsible for drug testing in the Federal workplace). Such testing is also common in the workplace environment where corporations in the US (and other parts of the world) use saliva as part of pre-employment and random drug testing policies.

General wellness is monitored by testing various steroid hormones in the laboratory. Home collection using a standardized saliva collection kit is common place and a large number of testing laboratories have appeared offering a multitude of test options for the "worried well". Tests include a range of male and female hormones including testosterone, estradiol, progesterone, cortisol and others. In these situations no "diagnosis" is provided on collected samples. Instead, a Medical Director from the laboratory will provide an indication of the levels of a specific target analyte in the saliva and make recommendations on suitable lifestyle changes or perhaps an imminent visit to the doctor.

The future for saliva testing also holds great promise since the publication of the entire salivary proteome by the Human Saliva Proteome Consortium, a group headed by Dr. David Wong from UCLA. The widespread publication of the identity of 1,166 proteins potentially implicated in disease progression will lead to the rapid growth in new applications for salivary diagnosis. Already in development are a diagnostic device for the rapid detection of the drug phenytoin, which uses a surface plasma resonance imaging instrument, an oral fluid Nanosensor test that measures four oral fluid markers as an indication of oral cancer and a lab-on-a-chip technology for point-of-care detection of salivary biomarkers in periodontitis, among a number of others. An excellent review of these and other new applications for oral fluid diagnostics was published following a landmark meeting of many researchers in the field at Lanier Lakes, Ga. USA in October 2006. The monograph published following the meeting is available from the New York Academy of Sciences.

Tools for oral fluid diagnosis may be categorized as one of two types. The first is diagnostic devices providing an immediate diagnosis or test result, so-called "point-of-care" or "near-patient" tests. This category includes the manual OraQuick® rapid HIV 1/2 antibody test that employs lateral flow immunochromatographic technology and the prototype Oral Fluid Nanosensor (OFNASET) Test device from Dr. David Wong's UCLA laboratory, which relies on microfluidics, nanotechnology in a hand-held reading device to potentially screen for oral cancer. This technology detects a series of four salivary molecular RNA markers. Another example among many others is a rapid point-of-care drug screening technology called RapiScan® from Cozart Biosciences (Abingdon, UK), which is used to screen would be drug offenders at the roadside using saliva samples. Many other rapid diagnostic products exist which require saliva sampling or testing, but such products are outside the scope of this application.

The other side of the market for salivary diagnostics involves the collection of oral fluids and the subsequent transportation of the samples to a laboratory, or other remote site where the testing is performed. Again many examples exist. Examples include the collection of oral samples for HIV testing for Public Health and also for insurance risk assessment, where oral specimens are collected using the OraSure® Oral Fluid Collection Device (OraSure Technologies, Bethlehem Pa., USA) and sent to a laboratory. Typically, specimens are analyzed using traditional ELISA technology for the detection of HIV, cotinine (nicotine), cocaine and others. Others include collection of saliva specimens for drug testing in the workplace environment for pre-employment purposes or random drug testing. In such situations saliva is collected using one of a number of available commercial saliva collection devices (including Intercept™ from OraSure Technologies, Bethlehem Pa., USA, Quanti-SAL™ from Immunalysis Corporation, Pomona Calif., USA, Aware Messenger™ from Calypte Biomedical, Lake Oswego, Oreg. USA and Salivette®, Sarstedt, Germany among others) then sent to a laboratory where a battery of drug tests including marijuana (THC), cocaine, opiates (heroin), methamphetamine, amphetamine, and phencyclidine is tested on the processed saliva. Similar practices are observed in Federal workplace and military drug testing environments.

A small industry has emerged for salivary hormone testing where laboratories provide saliva collection kits and a test menu for home users. Clients expectorate into a tube that is subsequently sent to a laboratory. As part of the service subjects are able to request testing for various steroid hormones as part of a general wellness screening panel. The results provide an indication of general health and wellness, without providing any definitive diagnosis.

Very recently a new industry has emerged for "personal genome" testing in what is termed the "consumer genetics" market. In this area saliva or buccal cell swab samples are collected in the home and sent to a laboratory and tested for specific genetic markers and single nucleotide polymorphisms (SNPs) that provide information on the parentage of the individual in question, predisposition to specific diseases, ancestry and other genetic information. The number of companies in this area is rapidly growing but at this time, the recognized market leading companies are 23 and Me, Navigenics, DeCode Genetics, Knome, Illumina, and Sciona. The convenience and non-invasiveness makes saliva very attractive for home testing/home collection products. Other applications in this market sector will be addressed in further detail below.

In general, multi-purpose saliva collection is facilitated using one of a number of commercially available saliva collection devices or by expectoration ("spitting") into a sample receptacle. A number of devices are now available to collect specimens and these include the OraSure® device (OraSure® Technologies), Aware Messenger™, Salivette, Omni•SAL® (Stat-Sure Diagnostics, Framingham, Mass., USA), ORACOL (Malvern Medical Developments, UK), Cozart Oral Swab (Cozart BioSciences, Abingdon, UK) and the Versi•SAL® device (Oasis Diagnostics® Corporation, Vancouver, Wash. USA). With the exception of the Versi•SAL® device, which provides the opportunity to use multiple absorbent materials, customized to specific applications, these products have limited applications. This is mainly due to limitations in the number and type of absorbent materials used to perform the saliva collection operation. While each of the above methodologies may be considered appropriate for certain applications in salivary testing, none of these devices is appropriate for the collection, stabilization, transportation and extraction of purified DNA from saliva. This in turn has restricted the use of salivary DNA for "downstream" applications particularly the potential use of saliva specimens for molecular diagnostic testing.

Molecular diagnostics is one of the fastest growing areas in the area of clinical and animal diagnostics. The current market for molecular diagnostics is estimated to be $3.2 billion (2007 figures) and forecast to reach $5.4 billion by 2012. In this area of clinical diagnostics traditional blood testing is by far the current method of choice. In current protocols, specimens are collected in a blood tube, usually by a trained phlebotomist, and sent to the laboratory. Upon receipt at the laboratory, the sample is initially separated from unwanted blood by-products then further purified prior to analysis. Blood samples contain potentially infectious agents and the cost of transportation can be expensive. In addition, all samples must be treated as infectious waste and disposed of according to recognized safety standards, which can also be costly. If a device was available to collect salivary DNA for clinical diagnostic testing this would offer several advantages over current blood testing algorithms and would be welcomed in clinical practice as a step forward. From the patient's perspective it would eliminate painful blood draws associated with current testing. In addition it would eliminate the need for a trained phlebotomist to draw the blood sample, as well as alleviate any potential for infection from tainted blood samples. Overall, saliva sampling is generally cheaper and does not require an additional pre-treatment step (as required for blood), to separate the required salivary component prior to analysis.

As described previously, there are a number of commercially available saliva collection devices on the market. In most cases, these devices incorporate some sort of absorbent material that is used to collect the saliva specimen. The sample is subsequently removed from the absorbent material using methods such as squeezing, centrifugation or simply soaking in a buffer to solubilize the target analytes. These devices work well for the collection of certain molecules such as infectious disease antibodies (including HIV, hepatitis B, hepatitis C and others), hormones, cancer biomarkers and drugs, for instance, but none of these may be applied to the collection and retrieval of DNA (Deoxy Ribonucleic Acid) or RNA (Ribo Nucleic Acid), which requires a device with very specific performance characteristics. This is due to an inherent property of current devices to bind DNA and RNA moieties to the fibers of the absorbent material used to collect the specimen. DNA binds tightly to the fibers and is not easily removed. Any effort to remove the DNA, cells using reagents, organic solvents usually results in denaturation of the DNA molecules and subsequently observed recoveries are poor.

Some of the above limitations have been overcome in a few devices that do successfully facilitate salivary DNA collection. Expectoration (spitting in a cup or other vessel) provides a saliva sample that can be successfully stabilized and purified through available methodologies to yield high quality DNA, and this method is in use in various testing strategies, however this method lacks adequate standardization (sample variability) and is not considered elegant or dignified.

Over the last few years other promising devices have emerged that are based upon modifications to the traditional expectoration technique. The most widely used of these is the OraGene® DNA device from DNA Genotek (Ottawa, Ontario, Canada). OraGene® is a more sophisticated way to collect saliva into a vessel to which is attached a screw-on cap. In the screw-on cap is a mixture of preservative buffers. Upon completion of the expectoration process, the cap is screwed onto the device releasing the preservative buffer, which drops into the saliva, is mixed by shaking and then acts to protect the integrity of the sample until processing and extraction can take place. The same company has recently perfected the OraGene® RNA device for the collection of RNA from oral fluid specimens. OraGene® RNA applies the same basic principles as used in the OraGene® DNA device. Invitek Gesellschaft für Biotechnik and Biodesign mbH (Invitek, Berlin, Germany) has come up with a similar tool, SaliGene® as an alternative "spit-in-a-cup" technology, which has additional application as a collector for stool or swab specimens (when coupled with specific extraction kits for these alternate specimen types). In the SaliGene®device, subjects expectorate into a modified collection tube until a pre-determined volume has been reached. A screw-cap with attached plunger is screwed in place and the plunger depressed causing a preservative/lysis buffer to flow into the collected saliva specimen. The sample of mixed preservatives and saliva is gently shaken then sent to a laboratory for further processing.

Researchers from Roswell Park describe the extraction of genomic DNA from saliva using the Qiagen (Hilden, Germany) QIAamp Kit on the Qiagen website. This work was reprinted from earlier work carried out in 1997. The QIAamp kit is one of a number of kits commercially available for DNA extraction from bodily fluids. In this case as in many others, expectoration was used to collect the saliva specimens.

In collecting specimens for diagnostic testing several criteria are important. Specimens need to be collected rapidly to eliminate any opportunity for sample degradation, and they must be removed rapidly from the point of collection and stabilized promptly for subsequent transportation purposes (if necessary). The specimen device used to collect saliva should be able to withstand temperature fluctuations and the rigors of shipping products by air or road allowing samples to arrive safely at the final destination laboratory, hospital or other remote facility. The sample so obtained should be stable for extended periods of time at ambient temperatures and also at −20 degrees Celsius for long-term storage.

Devices for DNA or RNA sample collection should be robust, transportable, capable of transporting a saliva sample (or other biological fluid) containing the DNA or RNA molecules to a laboratory or other remote facility and also to provide ready sample removal for subsequent extraction using a number of commercially available, off the shelf kits. The yield of DNA/RNA produced depends upon the particular application but should be sufficient for immediate application in testing kits provided by a multitude of manufacturers for infectious diseases, oncology, cardiovascular diseases, immunological disorders and many others. Literature reports suggest that a minimum of 10 μg of pure DNA should be collected and typically even larger quantities are required. For example, 100 μg or more of pure DNA would be a preferable sample quantity.

While the limited number of examples of salivary DNA devices described above provides methods for DNA/RNA collection and extraction, none of the above devices meet the market need for a simple, elegant, standardized and rapid method for the collection of biological fluids and other biological materials, with the specific purpose of extraction of DNA and RNA, for large scale implementation.

SUMMARY AND ADVANTAGES

An embodiment of the invention is a biological sample collection system comprising a biological sample collecting wand and a buffer container with a buffer solution. The biological sample collecting wand includes a handle and a sample collector detachably coupled to the handle. The sample collector include one or more sample protrusions, one or more sample apertures, or a combination thereof, at least the sample collector to removably insert into the buffer container.

The biological sample collection system of the present invention presents numerous advantages, including: (1) facilitation of the collection of a biological sample in sufficient quantity to conduct genetic testing and any other testing requiring DNA or RNA as the sample, e.g. microarrays, PCR, genotyping, and forensic sampling; (2) inexpensive construction; (3) handle and sample collector detachability feature to substantially protect the collected biological sample; (4) rapid sample collection time; (5) simple and more elegant collection method than traditional "spit-in-a-cup" technologies; (6) more amenable for large population studies and DNA collection by the patient/subject in the home; (7) rapid collection time reduces the possibility for introduction of any "foreign" DNA; (8) incorporation of a preservative/lysis buffer capable of protecting the integrity of the sample for long periods of time.

Additional advantages of the invention will be set forth in part in the description which follows, and in part will be obvious from the description, or may be learned by practice of the invention. The advantages of the invention may be realized and attained by means of the instrumentalities and combinations particularly pointed out in the appended claims. Further benefits and advantages of the embodiments of the invention will become apparent from consideration of the following detailed description given with reference to the accompanying drawings, which specify and show preferred embodiments of the present invention.

BRIEF DESCRIPTION OF THE DRAWINGS

The accompanying drawings, which are incorporated into and constitute a part of this specification, illustrate one or more embodiments of the present invention and, together with the detailed description, serve to explain the principles and implementations of the invention.

REFERENCE NUMBERS USED IN DRAWINGS

Turning now descriptively to the drawings, in which similar reference characters denote similar elements throughout the several views, the figures illustrate the fluid sample collection system of an embodiment of the present invention. With regard to the reference numerals used, the following numbering is used throughout the various drawing figures:

10 biological sample collection system
20 handle
22 handle rib member
24 handle neck
26 handle locking portion
28 handle locking detent
30 sample collector
32 sample cavity
34 sample protrusion
35 sample protrusion edge
36 sample aperture
40 sample collector handle receiver
42 receiver channel
44 receiver protrusion
50 buffer container
52 buffer container lid
60 biological sample collecting wand
62a absorbent material insert
62b absorbent material insert
62c absorbent material insert

DETAILED DESCRIPTION

Before beginning a detailed description of the subject invention, mention of the following is in order. When appropriate, like reference materials and characters are used to designate identical, corresponding, or similar components in differing figure drawings. The figure drawings associated with this disclosure typically are not drawn with dimensional accuracy to scale, i.e., such drawings have been drafted with a focus on clarity of viewing and understanding rather than dimensional accuracy.

In the interest of clarity, not all of the routine features of the implementations described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another. Moreover, it will be appreciated that such a development effort might be complex and time-consuming, but would nevertheless be a routine undertaking of engineering for those of ordinary skill in the art having the benefit of this disclosure.

FIGS. 1-6 show an embodiment of a biological sample collection system 10. More specifically, the embodiment is a biological sample collection system 10 to facilitate collection of biological specimens and particularly to facilitate collection of saliva, urine, and stool specimens from human or animal species for the purpose of extracting purified DNA and/or RNA. For example, DNA and/or RNA samples collected with the biological sample collection system 10 may be purified by one of a number of established sample purification kits yielding samples sufficiently pure and of high quality to be used in immediate testing protocols for any test requiring DNA or RNA samples. The purified DNA and/or RNA may thereafter have downstream application in testing methods including molecular diagnostics (e.g., polymerase chain reaction, genotyping, personal genomic testing, microarrays, and lab-on-a-chip technologies).

As shown in FIGS. 1-6, biological sample collection system 10 generally includes a biological sample collecting wand 60. In some embodiments, the biological sample collection system 10 includes a buffer container 50 with a detachable buffer container lid 52. The biological sample collecting wand 60 includes a handle 20 with a plurality of handle rib members 22, a handle neck 24 and a sample collector 30 that detachably couples to the handle neck 24. More specifically, the handle neck 24 further includes a handle locking portion 26 with a handle locking detent 28 formed therein to detachably engage a sample collector handle receiver 40 including a receiver channel 42 to receive the handle locking portion 26 and a receiver protrusion 44 to detachably engage the handle locking detent 28. When detachably joined, the handle 20 may be used to actuate the sample collector 30 to collect fluid, cellular, and/or tissue samples as will be described in more detail below.

The handle 20 of an embodiment may be formed with a size, shape, and/or configuration substantially suitable to manually manipulate the sample collector 30 to scrape, swipe, and/or swab the inside of the cheek(s), along the gum line(s) under the lip(s), across the tongue, and/or other saliva-bearing surface or surfaces of the human or animal to be sampled. Alternately, the handle 20 of an embodiment may be formed with a size, shape, and/or configuration substantially suitable to manually manipulate the sample collector 30 to scrape, swipe, and/or swab cellular-, saliva-, urine- and/or stool-bearing sources and/or surfaces. Accordingly, in an embodiment, the handle 20 may be formed of a plastic. For example, the handle 20 may be formed at least in part from polypropylene, polycarbonate, polyethylene, polytetrafluoroethylene (PTFE), enamel, nylon, ceramic, or a combination thereof that is substantially ridged to facilitate the sample collection with the sample collector 30 detachably coupled thereto. Further, in an embodiment, the plastic and/or other handle 20 material may be substantially heat- and/or chemical-resistant so that the biological sample collection system 10 of an embodiment may be sterilized (e.g., in an autoclave or chemiclave) prior to sample collection.

Figure 1A:
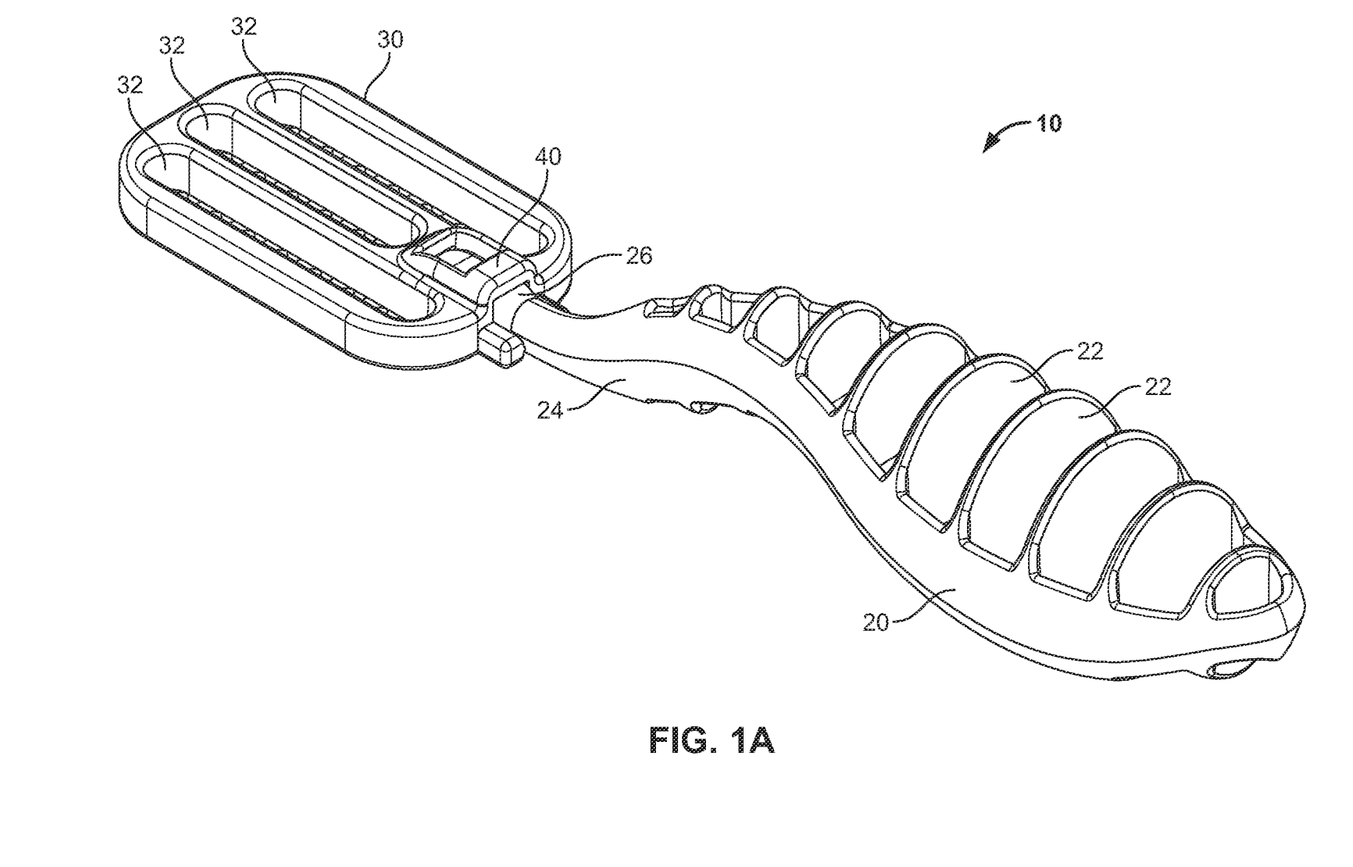
FIG. 1 shows a perspective view and a bottom view of an embodiment of the biological sample collecting wand.
Figure 1B:
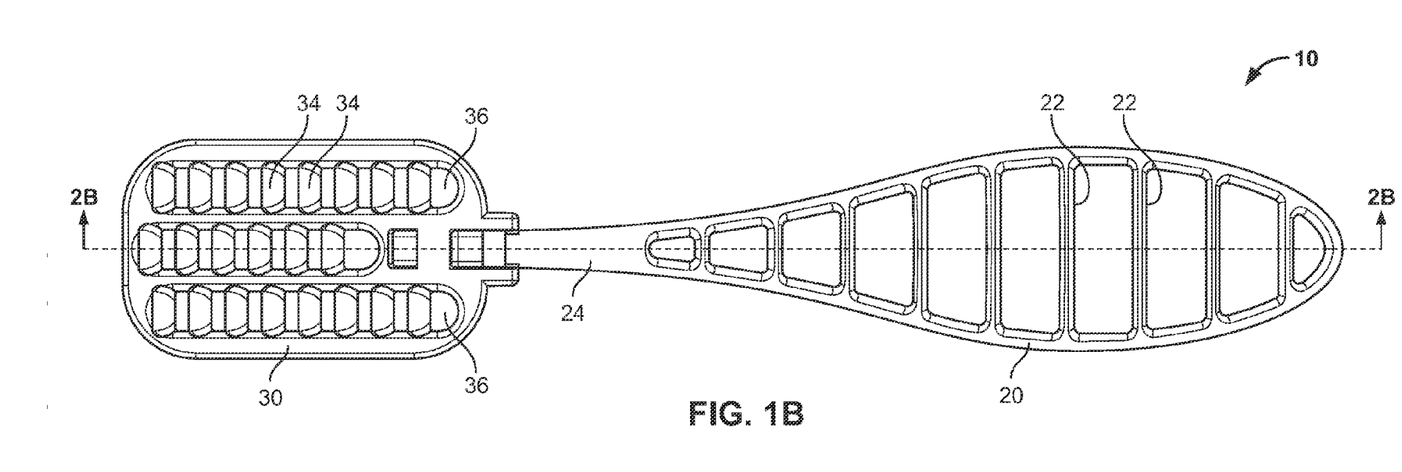
Figure 2A:
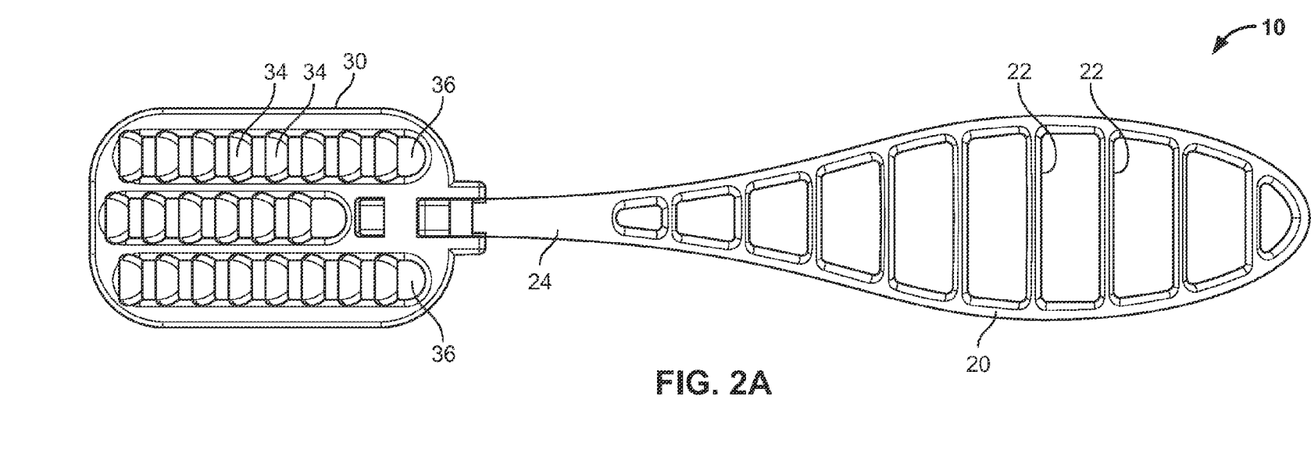
FIG. 2 shows a bottom view (2A), a side view (2C), and a section view (2B) of the biological sample collecting wand embodiment of FIG. 1.
Figure 2B:
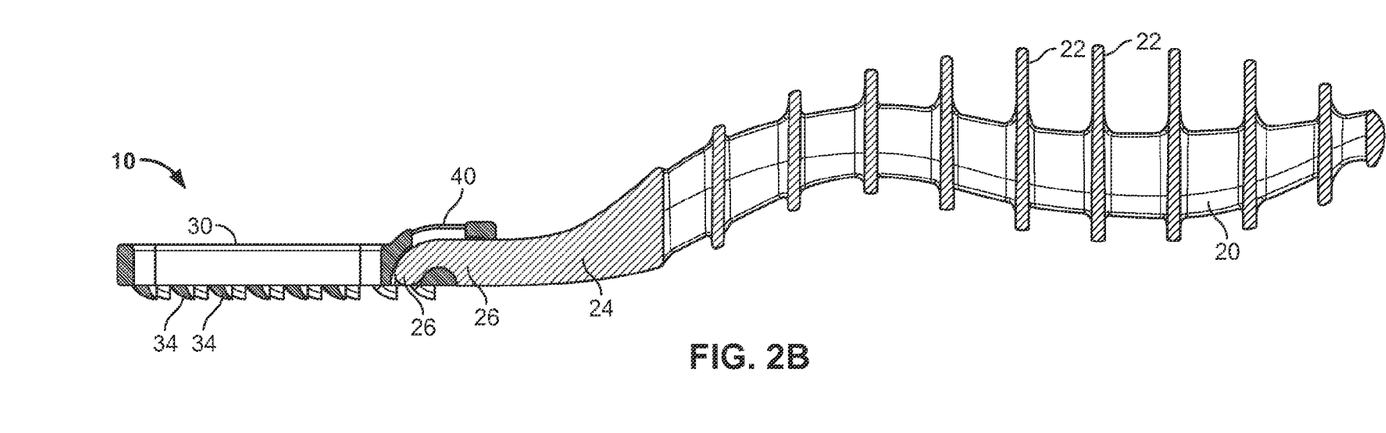
Figure 2C:
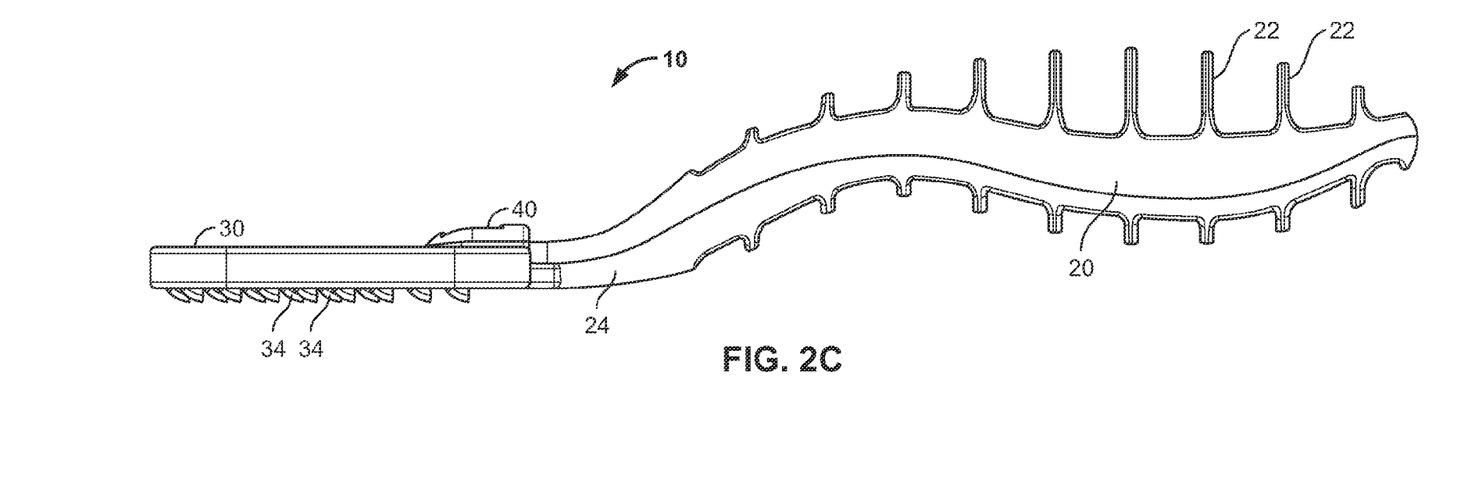
Figure 3A:
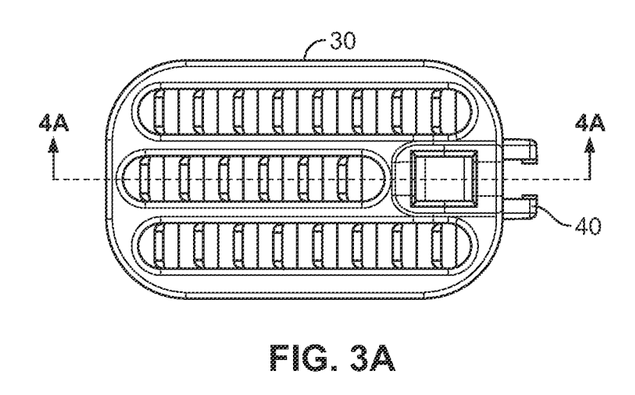
FIG. 3 shows a top view of the handle and a top view of the sample collector of an embodiment of the biological sample collecting wand.
Figure 3B:
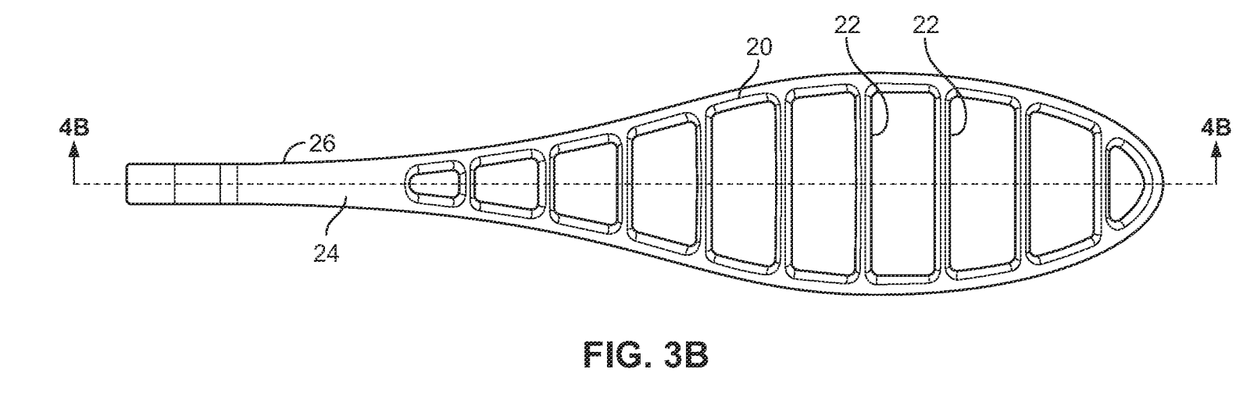

With reference to a longitudinal axis extending lengthwise through the handle 20 (e.g., section 2B-2B of FIG. 1), the handle 20 may be formed as a frame including two lateral sides joined by a plurality of handle rib members 22. The handle rib members 22 may have approximately circular or oval cross sections (i.e., perpendicular to the handle 20 longitudinal axis). More specifically, the handle rib members may be approximately egg-shaped with the prolate ellipsoid half extending away from, for example, the side of the biological sample collection system 10 including the sample protrusions 34 and the oblate ellipsoid half extending oppositely, for example, toward the side of the biological sample collection system 10 including the sample protrusions 34. Further, the handle rib members 22 may have varying sizes so that the effective thickness of the handle 20 (e.g., as gripped by a hand and/or one or more fingers thereof) varies across the longitudinal length of the handle 20. For example, the handle neck 24 may be substantially narrow after which the thickness of the handle 20 increases away from the sample collector 30. After reaching its widest and/or thickest region, the handle 20 may narrow toward its end distal from the sample collector 30.

Overall, the shape of the handle 20 as defined at least in part by the handle rib members 22 may provide the biological sample collection system 10 with substantial grip and control. Further, as the handle 20 including handle rib members 22 is approximately skeletal in their configuration, the handle 20 may exhibit substantial rigidity and effective handle thickness (e.g., as grasped by a sample collecting technician) without requiring a substantial volume of constituent material, for example if the handle 20 is molded from, at least in part, polypropylene, polycarbonate, polyethylene, polytetrafluoroethylene (PTFE), enamel, nylon, and/or a combination thereof.

The handle 20 may include one or more bends, angles, and/or arcuate portions. For example, the handle 20 may include a single bend and/or arc to form an angle in the handle 20. The handle 20 of an alternate embodiment may include two bends and/or arcs to form an offset in the handle 20. Further, the handle 20 may include the one or more bends at various locations along its length. More specifically, the handle 20 may include a bend and/or arc substantially adjacent the sample collector 30. For example, the handle neck 24 may include at least a bend and/or arc adjacent the sample collector 30. The handle 20 may include one or more additional bends and/or arcs along its length extending away from the sample collector 30.

Instead of or in addition to one or more specific bends or angles, the handle 20 may include one or more areas of curvature and/or one or more areas having an arcuate shape. The one or more bends, angles, curves, and the like formed in the handle 20 of an embodiment may aid locating the sample collector 30 adjacent a desired region of sample collection. For example, the handle 20 embodiments illustrated including an offset and/or curvature may aid the collection of samples from the buccal region(s) (i.e., toward the inside of the cheek) of the mouth. In an embodiment, the handle 20 may include two arcuate portions to form an approximate "S" shape in the handle 20. The approximate "S" shape of the handle may aid both the grip characteristics of the handle 20 as well as improved sample collection characteristics of the sample collector 30.

The one or more bends formed in handle 20 may be static bends integrally formed in the handle 20, or they may be dynamic bends that may further include a hinge, a living hinge, a pivot, or the like. The hinge and/or the pivot may include one or more springs or the like to bias the hinge and/or pivot toward a particular bend or angle. Further, if a living hinge, the properties (e.g., elasticity) of the handle 20 material may provide the bias toward a particular bend or angle.

The sample collector 30 of an embodiment may be formed of a similar plastic as the handle 20. For example, the sample collector 30 may be formed at least in part from polypropylene, polycarbonate, polyethylene, polytetrafluoroethylene (PTFE), enamel, nylon, ceramic, or a combination thereof. In an embodiment, the sample collector 30 and the handle 20 are formed substantially simultaneously (e.g., in the same plastic injection mold) as the handle 20. In an alternate embodiment, the sample collector 30 may be formed at least in part from a different material than the handle 20 that may be more suitable for sample collection.

In a further embodiment, the handle 20 and the sample collector 30 may be formed as two separate or discrete components that may be combined and/or removably engaged to form of the biological sample collection system 10. For example, and as will be described more fully below, the handle 20 and the sample collector 30 may be configured to detach from one another once a biological sample has been collected. In that manner, either the handle may be reused (for example, after sterilizing treatment in an autoclave and/or chemiclave) and/or the buffer container 50 size need only accommodate the sample collector 30 instead of both the handle 20 and the sample collector. The handle 20 and the sample collector 30 of en embodiment may alternately be formed substantially as two separate or discrete components but may further include a breakable portion, seam, intersection, or the like (not illustrated) that may substantially engage the handle 20 to the sample collector 30, and may thereafter be broken to separate the handle 20 from the sample collector 30.

As illustrated by FIGS. 1-4, the sample collector 30 may include one or more sample cavities 32, one or more sample protrusions 34, and one or more sample apertures 36, each corresponding to a sample protrusion 34. In an embodiment, the sample collector 30 may include three longitudinally elongated sample cavities 32 located on the top (i.e., away from the sample protrusions 34) of the sample collector 30. The plurality of sample protrusions 34 may be arranged in three rows, each row including approximately five to ten sample protrusions 34. More specifically, the middle row of sample protrusions 34 may include approximately six sample protrusions 34 while each lateral row may include approximately eight sample protrusions. The embodiments are not limited in this context.

Figure 4A:
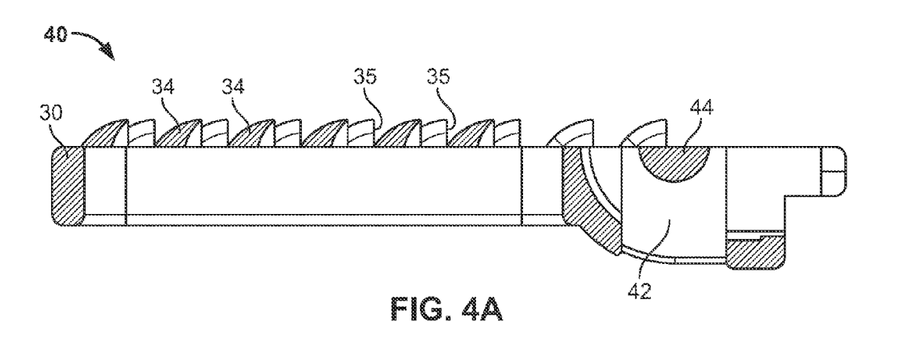
FIG. 4 shows section views 4A and 4B of FIG. 3.
Figure 4B:
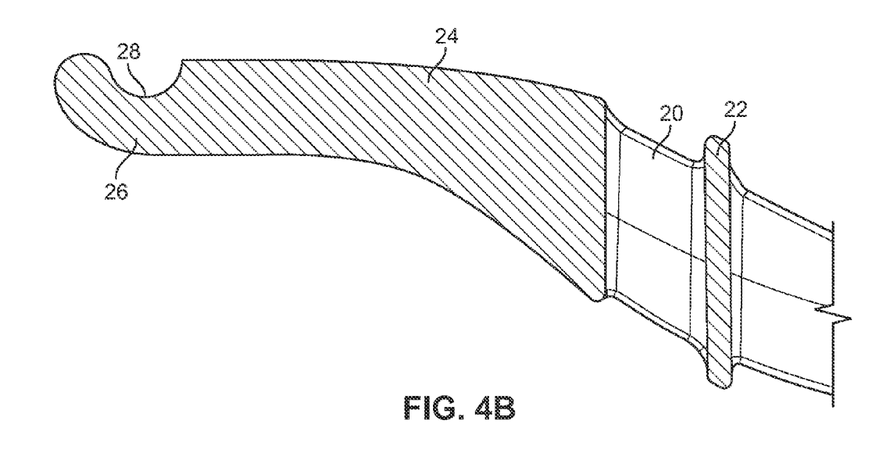

As illustrated in more detail in FIG. 4, the sample protrusions 34 of an embodiment may be shaped approximately like teeth. For example, each sample protrusion 34 may include a sample protrusion edge 35 that extends approximately perpendicularly from the surface of the sample collector 30. In an alternate embodiment, the sample protrusion edge 35 may extend from the surface of the sample collector at a non-perpendicular angle. More specifically, the sample protrusion edge 35 may define an angle with the surface of the sample collector 30 that is less than ninety degrees. With such a configuration, the sample protrusion 34 teeth may offer more bite depending on the type of biological sample to be collected (e.g., solid biological samples and/or liquid biological samples having substantial viscosity).

The sample protrusion 34 may taper from the distal tip of the sample protrusion 34 to the surface of the sample collector 30 approximately at an acute angle relative to the surface of the sample collector 30. More specifically, the sample protrusion may taper from the distal tip of the sample protrusion 34 to the surface of the sample collector 30 at approximately between a thirty and forty-five degree angle relative to the surface of the sample collector 30. In an embodiment, the sample protrusion 34 may taper approximately linearly. Alternately, the sample protrusion 34 may taper approximately in an arc.

A plurality of sample apertures 36 may be formed in the sample collector 30 corresponding to each of the sample protrusions 34. More specifically, the sample collector 30 may include a sample aperture 36 adjacent to each sample protrusion edge 35. When the sample collector 30 is drawn across a biological sample containing surface, the sample protrusion edges 35 (e.g., at an approximately perpendicular angle or less relative to the surface of the sample collector 30) may remove the sample material from the biological sample containing surface and direct the collected sample material through the sample apertures 36 to be accumulated in the one or more sample cavities 32. With such a configuration, the sample collector 30 is able to collect, accumulate, and reserve an amount and/or volume of sample material sufficient to perform genetic or other testing as introduced above.

Though not illustrated, one or more of the sample cavities 32 may be configured to accept an absorbent material therein. More specifically, the sample cavities 32 of an embodiment may each include an absorbent material insert. The absorbent material insert may be substantially secured in one or more of the sample cavities 32, or they may be configured to detach from the sample cavities 32 once a sample has been collected. In an embodiment, the absorbent material insert may aid the collection of in particular biological sample containing liquids (e.g., saliva, urine, reproductive fluids, and the like) by drawing, sucking, accumulating, and/or absorbing a biological sample containing liquid through the one or more sample apertures 36 and into the sample cavities 32. The biological sample containing liquid may be collected thereafter as described below with respect to the buffer container 50.

Though described with reference to discrete sample apertures 36 corresponding to each sample protrusion 34, an alternate embodiment may include a sample aperture 36 corresponding to each row of sample protrusions 34 and/or sample cavity 32. For example, each sample cavity 32 may extend at least in part completely through the sample collector 30 to form a sample aperture 36. For such a configuration, multiple sample protrusions 34 may span and/or straddle a single sample aperture 36. More specifically, each row of sample protrusions 34 may span and/or straddle a sample aperture 36 corresponding to the sample cavity 32 for that row of sample protrusions 34.

The sample collector 30 surface may include a rough texture and/or one or more surface features in addition to the sample protrusions 34 to scrape, swipe, and/or swab a biological sample from a sample source or sample substrate. Additionally, the sample protrusions 34 themselves may include a rough surface texture to facilitate sample collection as they scrape, swipe, and/or swab a biological sample containing surface. More specifically, the sample protrusions 34 may include edges and/or surfaces that include features to increase the ability with which the sample collector 30 may scrape or rake a surface to dislodge sample cells. For example, the edges of the sample protrusions 34 may be jagged, serrated, toothed, crenellated, or the like to scrape or rake a biological sample containing surface. The rough surface texture of the sample collector 30 may nevertheless not be too rough as to cause discomfort to the sample cell provider.

Further, in an embodiment, the sample collector 30 material may adsorb a biological sample and may create an adsorbate at the surface of the sample collector 30 from which a biological sample may be collected. Alternatively, the sample collector 30 may be formed of an absorbent material into which the sample fluid may diffuse and from which a sample may be collected. Additionally or alternatively, the sample collector 30 including sample protrusions 34 may be formed of a substantially hydrophilic material to attract biological samples, and in particular fluid biological samples. As noted above, in an embodiment, at least the sample collector 30 may be formed at least in part from polypropylene, polycarbonate, polyethylene, polytetrafluoroethylene (PTFE), enamel, nylon, ceramic, or a combination thereof to facilitate the collection of biological samples.

As introduced above, the handle 20 and the sample collector handle receiver 40 may be formed and/or detachably engaged to form the biological sample collection system 10. For example, and as illustrated in detail by FIG. 4, the handle neck 24 may further terminate at a handle locking portion 26 including a handle locking detent 28. The handle locking portion 26 of an embodiment including handle locking detent 28 may detachably engage the sample collector handle receiver 40. More specifically, the handle locking portion 26 may detachably insert into the receiver channel 42 and the receiver protrusion 44 may detachably engage the handle locking detent 28. In an embodiment, the receiver channel 42 may have an approximately arcuate shape to receive the handle locking portion 26. With such a configuration, the handle 20 may detachably engage the sample collector 30 substantially securely so that the handle 20 may apply pressure to the sample collector 30 to collect a biological sample. However, the detachable engagement of the handle 20 to the sample collector 30 may not be too secure to prevent and/or substantially interfere with the detachment of the handle 20 from the sample collector 30 once a sample has been collected. In an embodiment, the handle 20 may detachable engage the sample collector 30 in such a manner that, for example, a sample collecting technician does not have to touch or otherwise manipulate the sample collector 30 to detach it from the handle 20. The sample collecting technician may thereby avoid contaminating the sample collector 30 and any biological sample collected thereon.

As noted above, the biological sample collection system 10 may further include the buffer container 50 with the detachably engaged a buffer container lid 52. The buffer container 50 may include a buffer solution (not illustrated). The buffer solution provided, for example in buffer container 50, may incorporate various components available as off-the-shelf reagents. The buffer solution may contain a lysis reagent to lyse the cells and a preservative agent to stabilize the components in the collected biological sample for a period of several months. Guanidine is one agent known to preserve genetic samples (e.g., DNA and/or RNA) for long periods of time. Other buffer solutions may be provided in or with buffer container 50 consistent with an embodiment of biological sample collection system 10.

Figure 7:
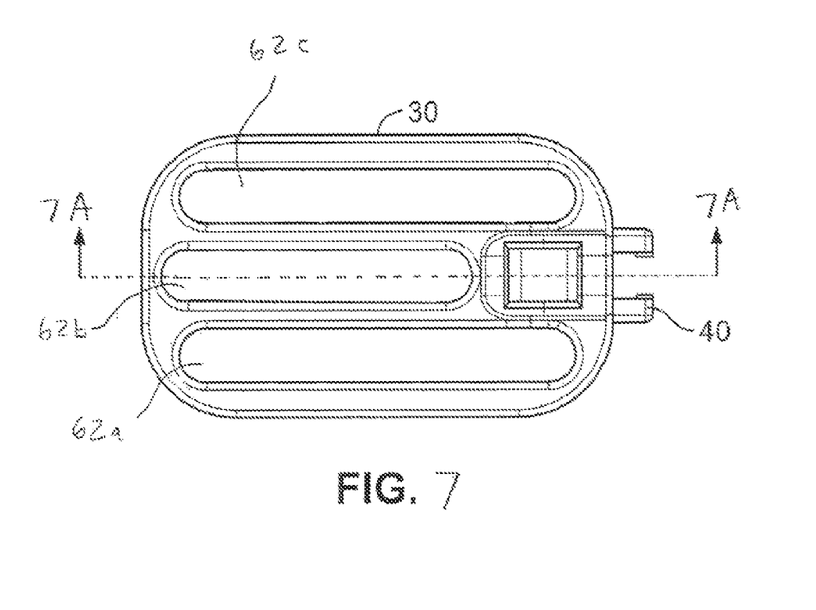
FIG. 7 shows a bottom view of an embodiment as in FIG. 3A further including absorbent material inserts.
Figure 7A:
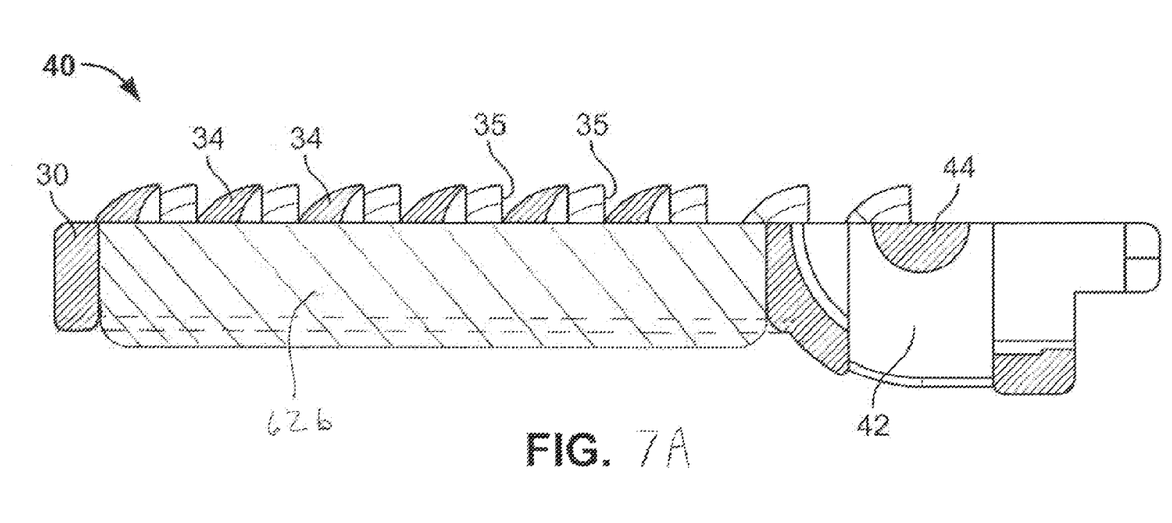
FIG. 7A shows a cutaway view of FIG. 7.

As illustrated in FIGS. 7-7A, one or more of the sample cavities 32 may be configured to accept an absorbent material therein. More specifically, the sample cavities 32 of an embodiment may each include an absorbent material insert 62a, 62b and/or 62c, respectively. The absorbent material insert 62a-c may be substantially secured in one or more of the sample cavities 32, or they may be configured to detach from the sample cavities 32 once a sample has been collected.

In an embodiment, the absorbent material insert 62a-c may aid the collection of in particular biological sample containing liquids (e.g., saliva, urine, reproductive fluids, and the like) by drawing, sucking, accumulating, and/or absorbing a biological sample containing liquid through the one or more sample apertures 36 and into the sample cavities 32. The biological sample containing liquid may be collected thereafter as described below with respect to the buffer container 50.

Further, though the biological sample collection system 10 of an embodiment is described including a sample collector 30 with three rows of sample protrusions 34, sample apertures 36, and sample cavities 32, it is to be understood that other configurations are possible. For example, depending on the subject from which the biological sample may be collected, the sample collector may include fewer or more rows of sample protrusions 34, sample apertures 36, and sample cavities 32. For example, a sample collector 30 configured for a pediatric subject may include only one or two rows of sample protrusions 34, sample apertures 36, and sample cavities 32. Further, each row may include fewer or more sample protrusions 34 than as illustrated in FIGS. 1-4. Further still, the size of the sample protrusions 34 may be altered. For example, for a pediatric subject, the sample protrusions 34 may be relatively smaller than as illustrated by FIGS. 1-4 so as to avoid irritating and/or injuring the pediatric subject from whom the biological sample is collected. Conversely, for example for a large animal subject, the strength, sturdiness, size, quantity, and/or configuration of the sample collector 30, sample protrusions 34, sample apertures 34, and/or sample cavities 32 may be increased. While the sample collector 30 of an embodiment may be configured for particular subjects, the handle 20 may or may not be correspondingly resized so that it may remain effective and/or comfortable to a sample collection technician.

Figure 5A:
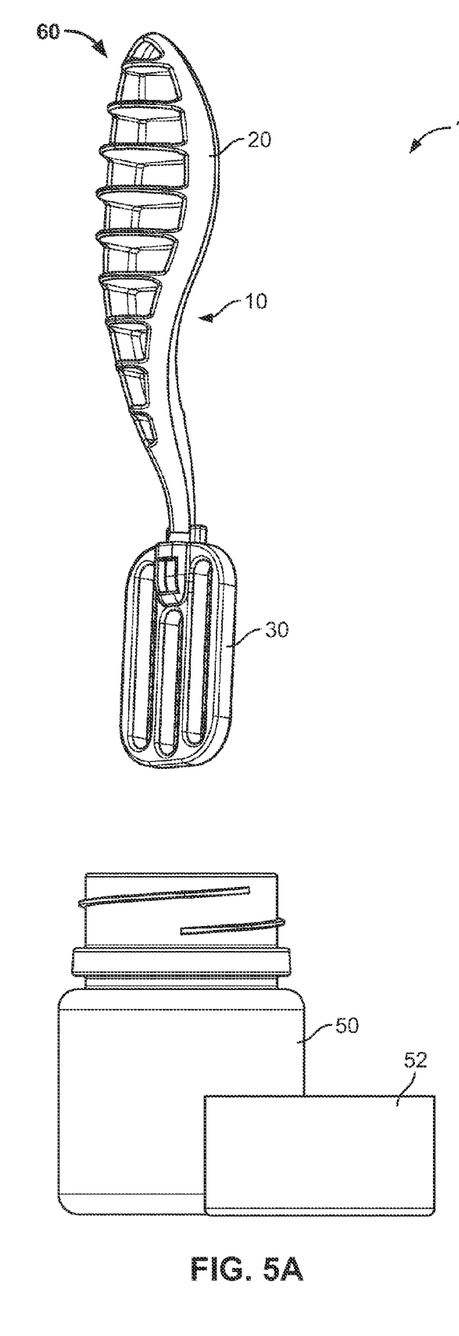
FIG. 5 shows an embodiment the biological sample collection system inserted into a buffer solution.
Figure 5B:
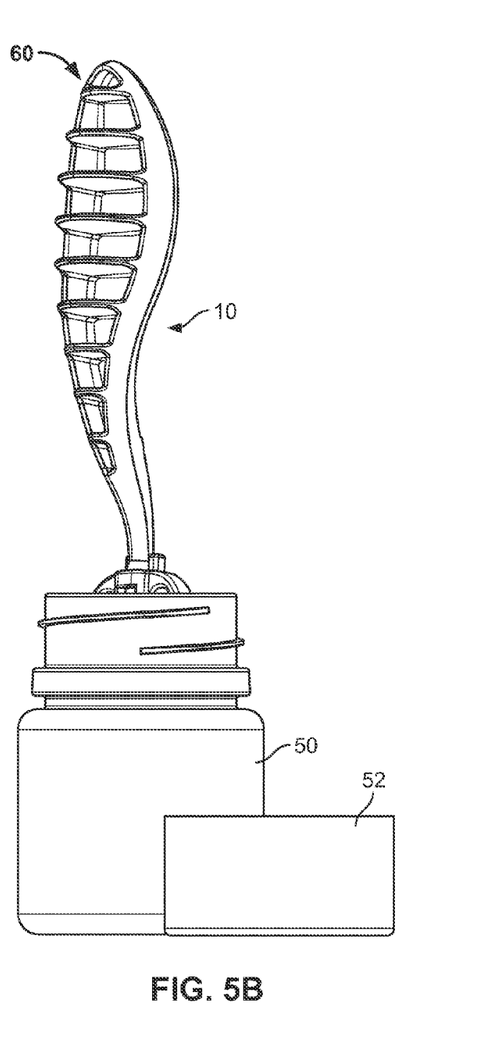
Figure 6A:
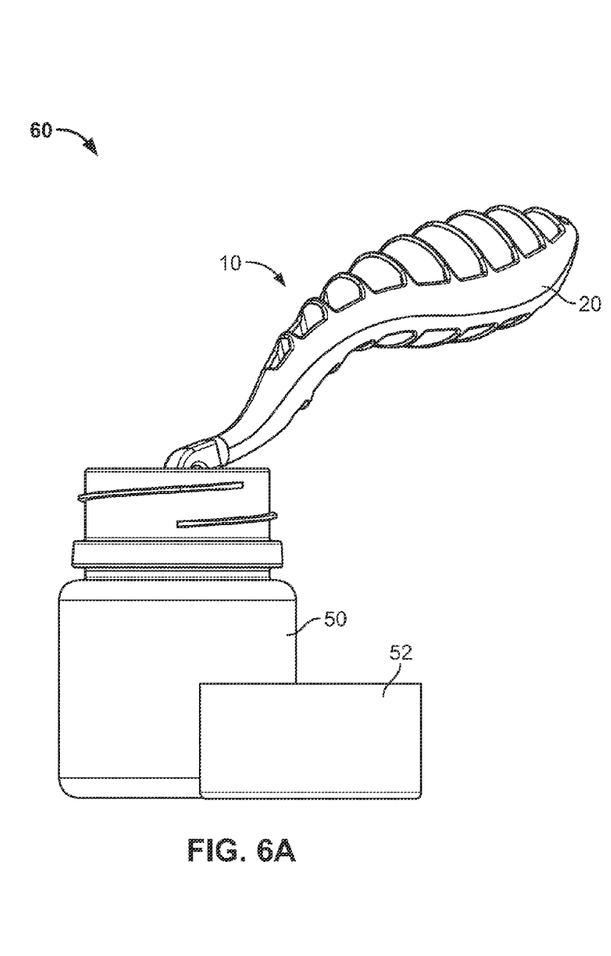
FIG. 6 shows an embodiment the biological sample collection system of FIG. 5 with the handle detached from the sample collector of the biological sample collecting wand.
Figure 6B:
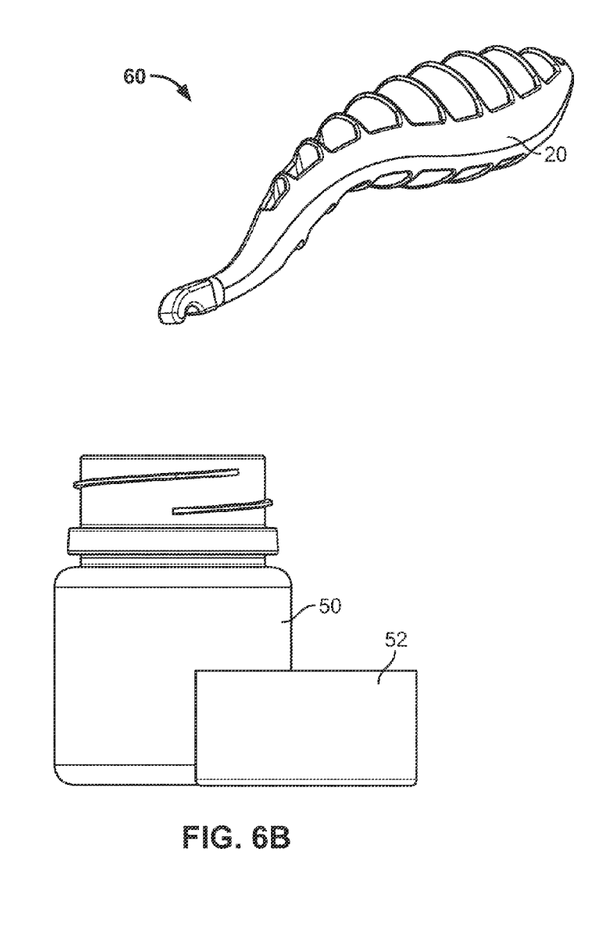

In operation in one embodiment as illustrated by FIGS. 5 and 6, to collect the biological sample, a sample collection technician or the like may grasp the handle 20 to scrape, swipe, and/or swab the sample collector 30 against, for example, a tongue or inside of a cheek to collect saliva. In an embodiment, the saliva may be collected by one or more sample protrusions 34, directed through one or more sample apertures 36, accumulated in one or more sample cavities 32, and/or a combination thereof. The sample collection technician may then insert at least the sample collector 30 into the buffer container 50. The sample collection technician may thereafter bend, rotate, torque, or otherwise apply pressure to the handle 20 to detach and/or break the handle 20 from the sample collector 30. In an embodiment, the sample collector 30 may fit completely within the buffer container 50. The sample collection technician may then attach the buffer container lid 52 to the buffer container 50, for example by screwing on the buffer container lid 52. Thereafter, the sample collection technician may then vigorously shake the buffer container 50 including the sample collector 30 to preserve the biological sample, for example saliva, from the sample collector 30. The buffer container 50 including the sample collector 30 contained therein may then be stored in an envelope, plastic bag, zip-lock plastic bag, or any other package (not illustrated) that may substantially secure (i.e., protect the buffer container 50 and sample collector 30 from contamination and to substantially prevent leakage and/or spillage should the buffer container 50 be damaged) and identify the buffer container 50 and the sample collector 30 it contains. Thereafter, the package including the buffer container 50 and sample collector 30 may be sent to a laboratory or other testing site for the purpose of DNA or RNA extraction and/or subsequent processing and analysis. In an embodiment, once detached the handle 20 may be discarded. In an alternate embodiment, the handle 20 may be detachably engaged to another sample collector 30, sterilized (for example in an autoclave or chemiclave) and reused. At any point during the biological sample collection by biological sample collection system 10, any unique identification information may be collected and recorded to uniquely identify the biological sample.

In other embodiments, a method of biological sample collection begins with a step of pooling saliva in the mouth of the subject. The next step is opening the buffer container 50 containing the buffer solution and setting down the buffer container 50 and buffer container lid 52 on a flat surface. The next step is taking the biological sample collection system 10 and placing it in the mouth of the subject with the sample protrusions 34 perpendicular to the inside of the subject's cheeks, towards the lower end of the inside of the subject's cheeks where the cheeks meet the gum line. The next step is placing a finger on the outside of the subject's cheeks to provide resistance while collecting the sample and raking the sample protrusions 34 along the inside of the subject's cheeks until the sample collector 30 is sufficiently loaded with saliva and cellular material. The sample collector 30 on the biological sample collection system 10 does not need to be saturated as additional cells will remain in free-flowing saliva in the mouth and will be collected by subsequent rinsing. Recommended raking time is approximately thirty seconds. The next step is removing the biological sample collection system 10 from the subject's mouth. For convenience, the subject may hold the biological sample collection system 10 in one hand while using the other hand to perform the next step. The next step is pouring the buffer solution contained in the buffer container 50 into the subject's mouth. The next step is swishing the buffer solution around the subjects mouth. Recommend time for swishing is 10-15 seconds. The subject should not swallow any of the buffer solution. The next step is picking up the buffer container 50 and expectorating as much of the buffer solution as possible back into the same the buffer container 50. The buffer solution is now enriched with saliva and epithelial cells containing DNA. The next steps are inserting the biological sample collection system 10 with the sample collector 30 pointing downwards into the buffer container 50 and twisting the biological sample collection system 10 in the neck of the buffer container 50 until the sample collector 30 drops off and into the buffer container 50. The next steps are discarding the handle 20 and screwing the buffer container lid 52 down tightly to secure the sample. The next step is shaking the buffer container 50 (now containing a mixture of buffer solution, saliva and cells) vigorously for 15 seconds to mix the buffer solution and the sample. The sample is now ready for immediate processing or for transportation to a laboratory where sample extraction may be performed.

Those skilled in the art will recognize that numerous modifications and changes may be made to the preferred embodiment without departing from the scope of the claimed invention. It will, of course, be understood that modifications of the invention, in its various aspects, will be apparent to those skilled in the art, some being apparent only after study, others being matters of routine mechanical, chemical and electronic design. No single feature, function or property of the preferred embodiment is essential. Other embodiments are possible, their specific designs depending upon the particular application. As such, the scope of the invention should not be limited by the particular embodiments herein described but should be defined only by the appended claims and equivalents thereof.

I claim:

1. A biological sample collection system comprising:
   a buffer container including a buffer solution, the buffer container including a resealable opening to receive the sample collector at least to the connector;
   a handle; and
   a sample collector detachably coupled to the handle at a connector and insertable into the buffer container at least to the connector, the sample collector having a front side to go against a tissue surface for collecting a sample, and an opposed back side, the sample collector including a plurality of sample protrusions disposed upon the front side,
   wherein each sample protrusion of the plurality of sample protrusions projects from the front side to a rounded terminal end and includes a convex exterior surface oriented away from the handle and a concave surface defining an exposed cavity oriented toward the handle, wherein at least a portion of the sample collector exposed cavities are in fluid communication with one or more sample apertures, the sample apertures extending through the sample collector from the front side through the back side to form open channels from the front to the back sides.

2. The biological sample collection system of claim 1, the connector comprising a handle a locking portion to detachably engage a sample collector handle receiver.

3. The biological sample collection system of claim 2, the locking portion further comprising
   a handle locking portion formed into the handle neck and a sample collector handle receiver,
   the sample collector handle receiver comprising a receiver channel defined by opposed first and second interior walls, parallel opposed first and second receiver arms extending from and in line with the first and second interior walls, each of the receiver arms including an opposing receiver protrusion spaced apart at a distance less than the width of the handle neck so as to tightly engage the handle neck, a transverse axle extending between the first and second interior walls, and a backing bridge extending transversely between the first and second interior walls but offset from the transverse axle to go against the handle neck side opposite the handle transverse channel when the handle locking portion is inserted into the sample collector handle receiver;
   the handle locking portion including a transverse channel disposed along the handle neck proximate a tapered terminal end and open on a first handle side, the open transverse channel adapted to conform to the transverse axle, the tapered terminal end adapted to fit snugly over the transverse axle and between the first and second interior walls.

4. The biological sample collection system of claim 1, the sample collector further comprising one or more sample cavities adjacent the one or more sample apertures to collect and accumulate a biological sample.

5. The biological sample collection system of claim 4, the one or more sample protrusions, one or more sample apertures, and one or more sample cavities to be configured in one or more rows in the sample collector.

6. The biological sample collection system of claim 5, wherein the sample apertures further comprise one or more elongated channels, at least one of the one or more elongated channels corresponding to and aligned with one of the one or more rows of sample protrusions.

7. The biological sample collecting wand of claim 4, further comprising:

one or more absorbent material inserts coupled to the sample collector portion within the respective one or more sample cavities.

8. The biological sample collection system of claim 1, the buffer container further comprising a buffer container lid.

9. The biological sample collection system of claim 1 further comprising a buffer container lid to detachably engage the buffer container.

10. The biological sample collecting wand of claim 1, further comprising:
one or more absorbent material inserts coupled to the sample collector portion.

11. A biological sample collecting wand comprising:
a handle; and
a sample collector detachably engaged to the handle, the sample collector having a front side to go against a tissue surface for collecting a sample, and an opposed back side, the sample collector including a plurality of sample protrusions disposed upon the front side,
wherein each sample protrusion of the plurality of sample protrusions projects from the front side to a rounded terminal end and includes a convex exterior surface oriented away from the handle and a concave surface defining an exposed cavity oriented toward the handle, wherein at least a portion of the sample collector exposed cavities are in fluid communication with one or more sample apertures, the sample apertures extending through the sample collector from the front side through the back side to form open channels from the front to the back sides.

12. The biological sample collecting wand of claim 11 wherein the protrusions are substantially teeth shaped.

13. The biological sample collecting wand of claim 11 wherein the sample protrusions, the sample apertures, or combination thereof are arranged in one or more rows.

14. The biological sample collecting wand of claim 13 wherein the sample apertures further comprise one or more elongated channels, at least one of the one or more elongated channels corresponding to and aligned with one of the one or more rows of sample protrusions.

15. The biological sample collecting wand of claim 14, further comprising:
one or more absorbent material inserts coupled to the sample collector portion within the respective one or more sample cavities.

16. The biological sample collecting wand of claim 11, the handle further comprising a locking portion including a locking detent.

17. The biological sample collecting wand of claim 16, the sample collector further comprising
a handle locking portion formed into the handle neck and a sample collector handle receiver,
the sample collector handle receiver comprising a receiver channel defined by opposed first and second interior walls, parallel opposed first and second receiver arms extending from and in line with the first and second interior walls, each of the receiver arms including an opposing receiver protrusion spaced apart at a distance less than the width of the handle neck so as to tightly engage the handle neck, a transverse axle extending between the first and second interior walls, and a backing bridge extending transversely between the first and second interior walls but offset from the transverse axle to go against the handle neck side opposite the handle transverse channel when the handle locking portion is inserted into the sample collector handle receiver;
the handle locking portion including a transverse channel disposed along the handle neck proximate a tapered terminal end and open on a first handle side, the open transverse channel adapted to conform to the transverse axle, the tapered terminal end adapted to fit snugly over the transverse axle and between the first and second interior walls.

18. The biological sample collecting wand of claim 11, the handle and the sample collector further comprising polypropylene, polycarbonate, polyethylene, polytetrafluoroethylene (PTFE), enamel, nylon, ceramic, or a combination thereof.

19. The biological sample collecting wand of claim 11, further comprising:
one or more absorbent material inserts coupled to the sample collector portion.

* * * * *